United States Patent
Iwase et al.

(10) Patent No.: US 10,967,134 B2
(45) Date of Patent: Apr. 6, 2021

(54) INJECTION NEEDLE ASSEMBLY AND MEDICINE INJECTION DEVICE

(71) Applicant: TERUMO KABUSHIKI KAISHA, Tokyo (JP)

(72) Inventors: Yoichiro Iwase, Kanagawa (JP); Junichi Ogawa, Yamanashi (JP); Kouichi Tachikawa, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 420 days.

(21) Appl. No.: 15/805,740

(22) Filed: Nov. 7, 2017

(65) Prior Publication Data

US 2018/0056010 A1 Mar. 1, 2018

Related U.S. Application Data

(60) Division of application No. 14/065,151, filed on Oct. 28, 2013, now abandoned, which is a continuation of
(Continued)

(30) Foreign Application Priority Data

Apr. 28, 2011 (JP) .................................. 2011-101225

(51) Int. Cl.
*A61M 5/32* (2006.01)
*A61M 5/34* (2006.01)
(Continued)

(52) U.S. Cl.
CPC ........ *A61M 5/3293* (2013.01); *A61M 5/3287* (2013.01); *A61M 5/345* (2013.01);
(Continued)

(58) Field of Classification Search
CPC .. A61M 5/3146; A61M 5/3293; A61M 5/345; A61M 5/425; A61M 2005/1402; A61M 1/3643
See application file for complete search history.

(56) References Cited

U.S. PATENT DOCUMENTS 2,701,566 A   2/1955  Krug
3,324,854 A   6/1967  Weese
(Continued)

FOREIGN PATENT DOCUMENTS

JP   2000-037456 A   2/2000
JP   2000-062100 A   2/2000
(Continued)

OTHER PUBLICATIONS

The First Office Action dated Feb. 16, 2015, by the State Intellectual Property Office of People's Republic of China in corresponding Chinese Patent Application No. 201280020046.9, and an English translation of the Office Action. (15 pages).
(Continued)

*Primary Examiner* — Manuel A Mendez
*Assistant Examiner* — Justin L Zamory
(74) *Attorney, Agent, or Firm* — Buchanan Ingersoll & Rooney PC

(57) ABSTRACT

A needle tube having a needle tip for puncturing skin; a needle hub; and a fluid-draining portion for enabling draining of a medicine. The needle hub includes: a retention part (first member) for retaining the needle tube; an insertion part into which the output portion of a syringe is inserted; and a flange-like skin contact portion that is disposed in a manner so as to cover an area surrounding the needle tube and makes contact with and/or faces the skin when a living body is punctured with the needle tube. The fluid-draining portion is disposed in the skin contact portion of the needle hub and
(Continued)

enables a user to drain the medicine that has spilled when removing air and is held in the skin contact portion.

9 Claims, 4 Drawing Sheets

Related U.S. Application Data application No. PCT/JP2012/055093, filed on Feb. 29, 2012.

(51) Int. Cl.
*A61M 5/42* (2006.01)
*A61M 5/46* (2006.01)

(52) U.S. Cl.
CPC ............ *A61M 5/329* (2013.01); *A61M 5/347* (2013.01); *A61M 5/425* (2013.01); *A61M 5/46* (2013.01); *A61M 2205/0222* (2013.01); *A61M 2205/0238* (2013.01)

(56) References Cited

U.S. PATENT DOCUMENTS

| | | | |
|---|---|---|---|
| 3,472,227 A | 10/1969 | Burke | |
| 3,523,531 A | 8/1970 | Burke | |
| 3,523,532 A | 8/1970 | Burke | |
| 3,556,099 A | 1/1971 | Knight | |
| 3,756,235 A | 9/1973 | Burke | |
| 3,903,887 A | 9/1975 | Antoshkiw | |
| 4,240,426 A | 12/1980 | Akhavi | |
| 4,240,433 A | 12/1980 | Bordow | |
| 4,568,346 A | 2/1986 | Van Dijk | |
| 4,795,445 A | 1/1989 | Jensen | |
| 4,958,625 A | 9/1990 | Bales | |
| 4,966,589 A | 10/1990 | Kaufman | |
| 5,108,378 A | 4/1992 | Firth | |
| 5,171,214 A | 12/1992 | Kolber | |
| 5,186,972 A * | 2/1993 | Williams | ............... A61B 17/00 427/2.28 |
| 5,197,953 A | 3/1993 | Colonna | |
| 5,250,037 A | 10/1993 | Bitdinger | |
| 5,364,362 A | 11/1994 | Schulz | |
| 5,393,497 A | 2/1995 | Haber | |
| 5,976,102 A | 11/1999 | Epstein | |
| 5,984,890 A | 11/1999 | Gast | |
| 6,200,291 B1 | 3/2001 | Di Pietro | |
| 6,503,229 B2 | 1/2003 | King | |
| 6,569,123 B2 | 5/2003 | Alchas | |
| 6,607,509 B2 | 8/2003 | Bobroff | |
| 6,666,844 B1 | 12/2003 | Igo | |
| 6,776,776 B2 | 8/2004 | Alchas | |
| 6,939,322 B2 | 9/2005 | Crank | |
| 7,438,703 B2 | 10/2008 | Barrus | |
| 7,556,615 B2 * | 7/2009 | Pettis | ...................... A61M 5/28 604/117 |
| 7,794,445 B2 | 9/2010 | Dalton | |
| 8,876,764 B2 | 11/2014 | Tsals | |
| 2001/0039400 A1 | 11/2001 | Lubrecht | |
| 2001/0056265 A1 | 12/2001 | Heinz | |
| 2002/0077599 A1 | 6/2002 | Wojcik | |
| 2003/0050602 A1 | 3/2003 | Pettis et al. | |
| 2003/0097098 A1 * | 5/2003 | Lavi | ...................... A61M 5/158 604/263 |
| 2004/0147901 A1 | 7/2004 | Py | |
| 2007/0060904 A1 | 3/2007 | Vedrine et al. | |
| 2007/0093760 A1 | 4/2007 | Wexler | |
| 2007/0118077 A1 | 5/2007 | Clarke et al. | |
| 2008/0300542 A1 * | 12/2008 | Kitani | ................... A61M 39/26 604/131 |
| 2009/0082732 A1 | 3/2009 | Hillman | |
| 2009/0234246 A1 | 9/2009 | Usui | |
| 2010/0137831 A1 | 6/2010 | Tsals | |
| 2011/0077602 A1 | 3/2011 | Yokota et al. | |
| 2011/0224609 A1 | 9/2011 | Tsals | |
| 2012/0179113 A1 | 7/2012 | Yokota et al. | |

FOREIGN PATENT DOCUMENTS

| | | |
|---|---|---|
| JP | 2004-175822 A | 6/2004 |
| JP | 2008-532701 A | 8/2008 |
| JP | 4383168 B2 | 12/2009 |
| WO | WO 2007/063828 A1 | 6/2007 |
| WO | 2011/040263 A1 | 4/2011 |
| WO | WO 2011/040221 A1 | 4/2011 |

OTHER PUBLICATIONS

The Second Office Action dated Sep. 22, 2015, by the State Intellectual Property Office of People's Republic pf China in corresponding Chinese Patent Application No. 201280020046.9, and an English translation of the Office Action. (13 pages).

Office Action (Notification to Grant Patent Right for Invention) dated Dec. 29, 2015, by the State Intellectual Property Office of People's Republic of China in corresponding Chinese Patent Application No. 201280020046.9, and an English translation of the Office Action. (3 pages).

Office Action (Decision of Refusal) dated Feb. 9, 2016, by the Japanese Patent Office in corresponding Japanese Patent Application No. 2013-511962, and an English translation of the Office Action (10 pages).

Office Action (Notification of Reasons for Refusal) dated Oct. 19, 2015, by the Japanese Patent Office in corresponding Japanese Patent Application No. 2013-511962, and an English translation of the Office Action. (9 pages).

Office Action (Decision to Grant Patent) dated May 30, 2016, by the Japanese Patent Office in corresponding Japanese Patent Application No. 2013-511962, and an English translation of the Office Action. (6 pages).

Extended European Search Report dated Sep. 4, 2014, by the European Patent Office in corresponding European Patent Application No. 12776467.8-1662. (6 pages).

Communication pursuant to Article 94(3) EPC dated Aug. 21, 2017, by the European Patent Office in corresponding European Patent Application No. 12 776 467.8-1664. (4 pages).

International Search Report (PCT/ISA/210) dated Jun. 5, 2012, by the Japanese Patent Office as the International Searching Authority for International Application No. PCT/JP2012/055093.

The extended European Search Report dated Sep. 4, 2014, in corresponding European Patent Office Application No. 12776467.8-1662 (6 pgs).

* cited by examiner

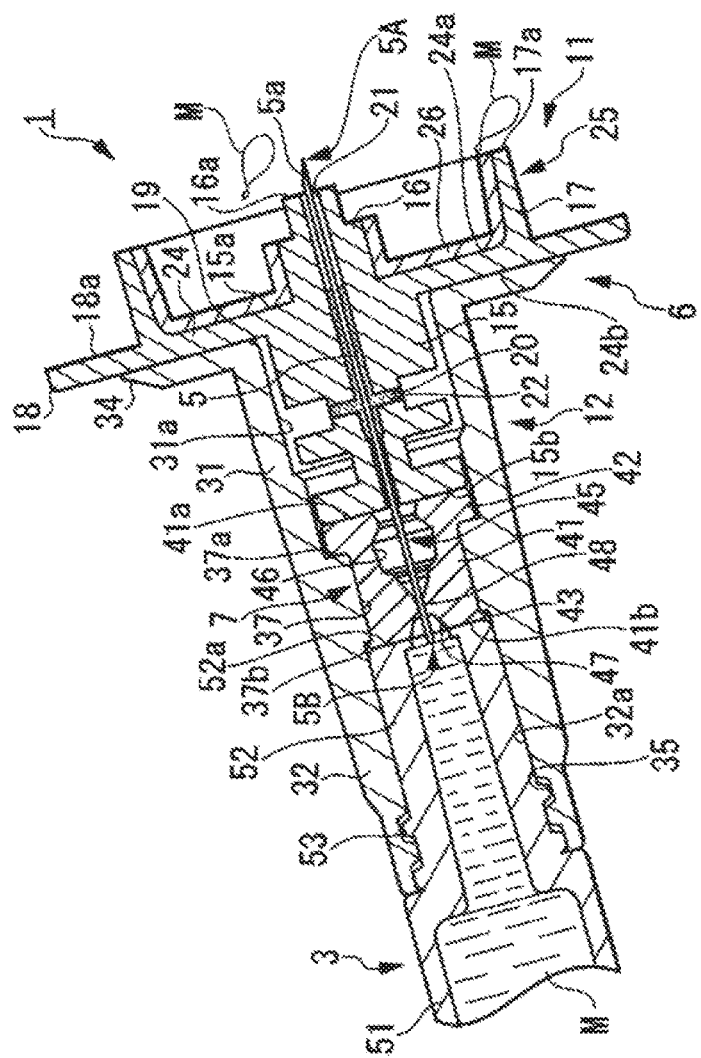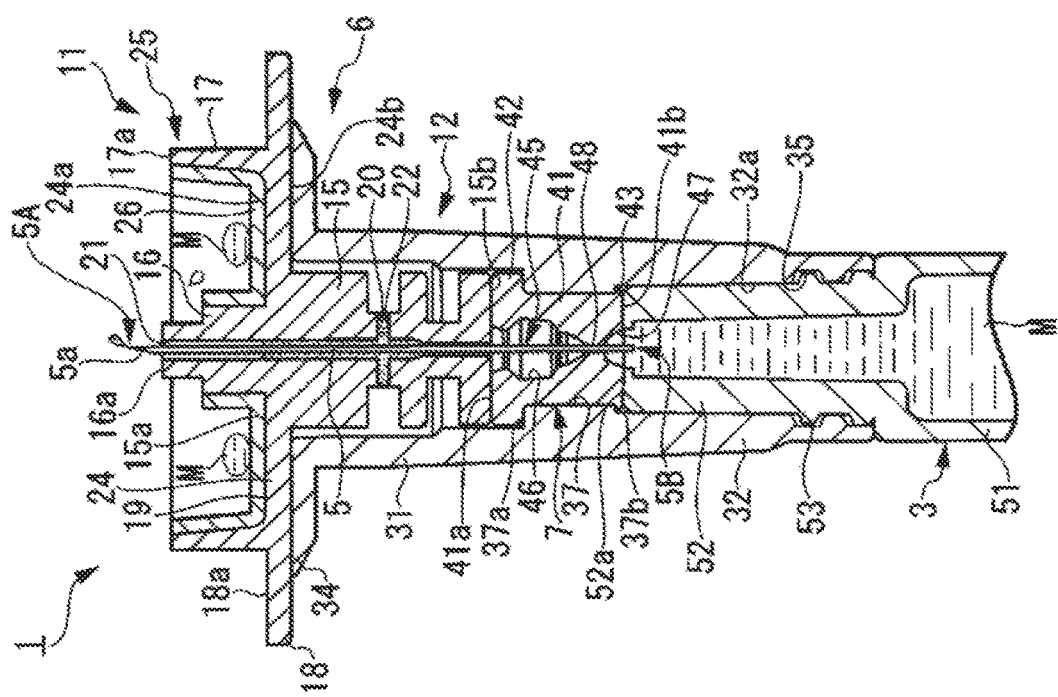

INJECTION NEEDLE ASSEMBLY AND MEDICINE INJECTION DEVICE

CROSS-REFERENCES TO RELATED APPLICATIONS

This application is a divisional of U.S. application Ser. No. 14/065,151, filed Oct. 28, 2013, which claims priority as a continuation application under 35 U.S.C. § 120 to International Application No. PCT/JP2012/055093 filed on Feb. 29, 2012, designating the U.S., and which claims priority to Japanese Application No. 2011-101225 filed on Apr. 28, 2011, the entire content of all being incorporated herein by reference.

TECHNICAL FIELD

The present invention relates to an injection needle assembly and a medicine injection device, which have a skin contact portion that is disposed to cover the area surrounding a needle tube and which makes contact with and/or faces the skin.

BACKGROUND ART

Conventionally, an injection needle assembly is provided with a skin contact portion that allows adjustment of the depth of a needle puncturing in order to stably puncture the skin. Such a configuration makes it possible to reliably penetrate the injection needle to a target depth. Further, such capability of stable puncturing enables stable administration of a medicine into the skin, as described in Japanese Patent Application Laid-Open No. 2000-037456. An injection needle assembly is connected to a syringe that is to be filled with a medicine, and thus a medicine injection device is assembled.

Air must be exhausted from the syringe, however, before introducing a medicine into it. Thus, a user of the medicine injection device must first perform a procedure to exhaust the air from the syringe, and then introduce the medicine into the device. This procedure or step is referred to as removal of air ("air removal" hereinafter) in which the air contained in the syringe is exhausted.

According to the injection needle assembly set forth in the above-noted Japanese Patent Application Laid-Open No. 2000-037456, a cylindrical skin contact portion is connected to a needle hub. The skin contact portion is disposed to cover a needle tube, but allows a space between the needle tube and the skin contact portion. Hence, when performing the air removal procedure using such a configured injection needle assembly, not only is the air contained in the syringe exhausted, but the medicine filled in the syringe may also spill from the needle tube and there is a risk of the medicine being held in the space between the skin contact portion and the needle tube.

A problem has thus arisen because the medicine staying in the space between the skin contact portion and the needle tube contacts or attaches to the skin of a user, and causes discomfort to the user when administering the medicine in the injection needle.

SUMMARY

In consideration of the aforementioned problem, the disclosure herein provides an injection needle assembly and a medicine injection device, which enable a user to easily drain the medicine that has been spilled during air removal and which is held in a skin contact portion.

More particularly, an exemplary embodiment of an injection needle assembly according to the disclosure includes: a needle tube having a needle tip for puncturing the skin; a needle hub; and a fluid-draining portion for enabling a medicine to be drained. The needle hub includes: a retention part for retaining the needle tube; an insertion part into which an output portion of a syringe is inserted; and a flange-like skin contact portion that is disposed in a manner so as to cover an area surrounding the needle tube and which makes contact with and/or faces the skin when a living body is punctured with the needle tube. Further, the fluid-draining portion is disposed in the skin contact portion of the needle hub.

A medicine injection device according to an exemplary embodiment of the disclosure includes: a syringe having an output portion; a needle tube having a needle tip for puncturing the skin; a needle hub; and a fluid-draining portion for enabling a medicine to be drained. The needle hub includes: a retention part for retaining the needle tube; an insertion part into which the output portion of the syringe is inserted; and a flange-like skin contact portion that is disposed in a manner so as to cover an area surrounding the needle tube and which makes contact with and/or faces the skin when a living body is punctured with the needle tube. Further, the fluid-draining portion is disposed in the skin contact portion of the needle hub.

The injection needle assembly and the medicine injection device according to the disclosure enable a user to easily drain any medicine staying in the skin contact portion by virtue of the fluid-draining portion disposed in the skin contact portion of the needle hub. As a result, the medicine that has been spilled when performing the air removal procedure can be drained before administering the medicine, and thus it is possible to prevent the medicine being held in the skin contact portion from contacting the user.

BRIEF DESCRIPTION OF THE DRAWINGS

Other purposes, features and characteristics of the injection needle assembly and medicine injection device will become more clear by referring to the following detailed description considered with reference to the attached drawings, wherein:

FIGS. 4A and 4B are cross-sectional views showing a process of draining a medicine in the first exemplary embodiment of the medicine injection device according to the disclosure herein, with FIG. 4A being a cross-sectional view showing a state where a medicine stays in the fluid-draining portion of a skin contact portion, and FIG. 4B being a cross-sectional view showing a state where the medicine staying in the fluid-draining portion of the skin contact portion is drained.

DETAILED DESCRIPTION

Figure 1:
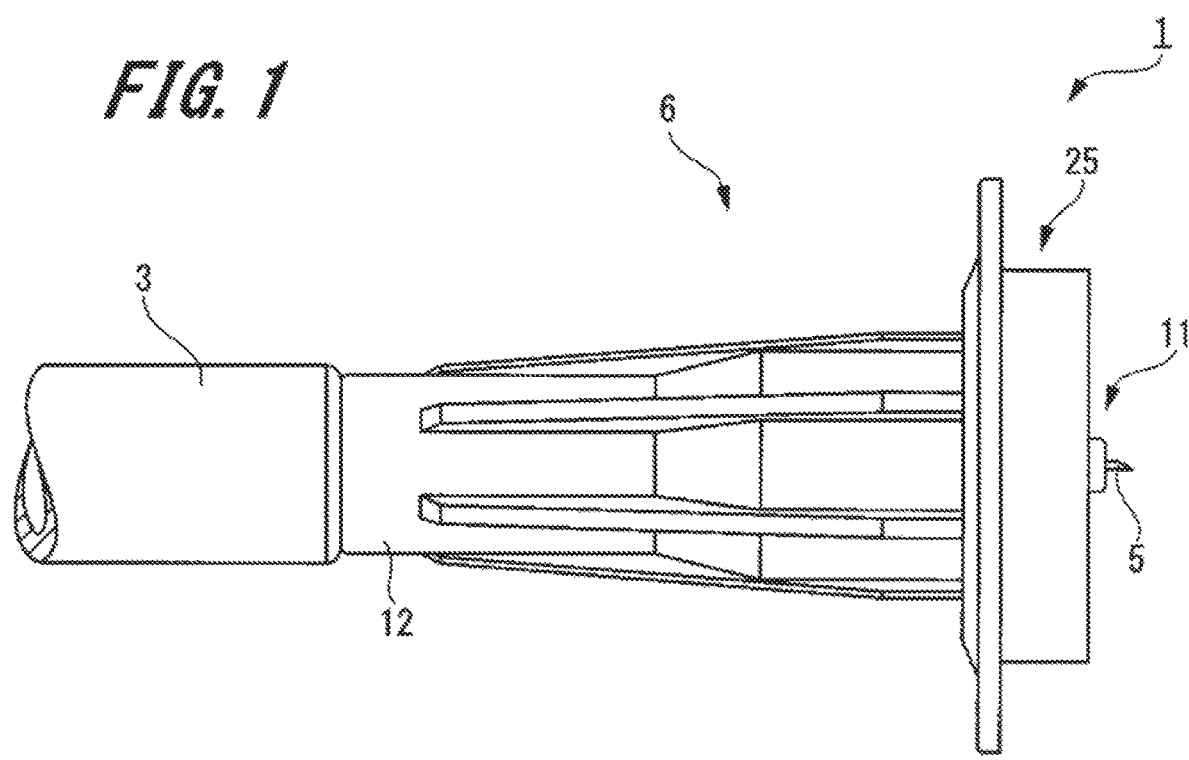
FIG. 1 is a side elevational view showing a first exemplary embodiment of a medicine injection device according to the disclosure herein.

Exemplary embodiments of an injection needle assembly and a medicine injection device according to the disclosure herein are described below with reference to FIGS. 1 through 5. It is noted that the same reference numerals are attached to a common components in the accompanying figures. It is further noted that the disclosure is in no way restrained by the following exemplary embodiments.

An injection needle assembly and a medicine injection device according to a first exemplary embodiment of the disclosure are described with reference to FIG. 1 and FIG. 2.

As shown in FIG. 1, a medicine injection device 1 is used for injecting a medicine into an upper skin layer by puncturing a skin surface with a needle tip. The medicine injection device 1 includes an injection needle assembly 2, and a syringe 3 to which the injection needle assembly 2 is detachably attached.

The skin includes three regions, that is, epidermis, dermis and subcutis. The epidermis is a layer of 50 to 200 μm from the outermost skin surface, while the dermis is a layer of 1.5 to 3.5 mm continuing from and beneath the epidermis. Influenza vaccines are generally administered with a subcutaneous or intramuscular injection, and therefore are injected to a lower layer of the skin or a deeper region thereof.

Considerations are being given, however, to injecting the influenza vaccines into an upper skin layer since such layer has a large number of immune-competent cells and would thereby decrease the required injection volume of the vaccines. It is noted that the upper skin layer here means the epidermis and dermis of the skin.

Figure 2:
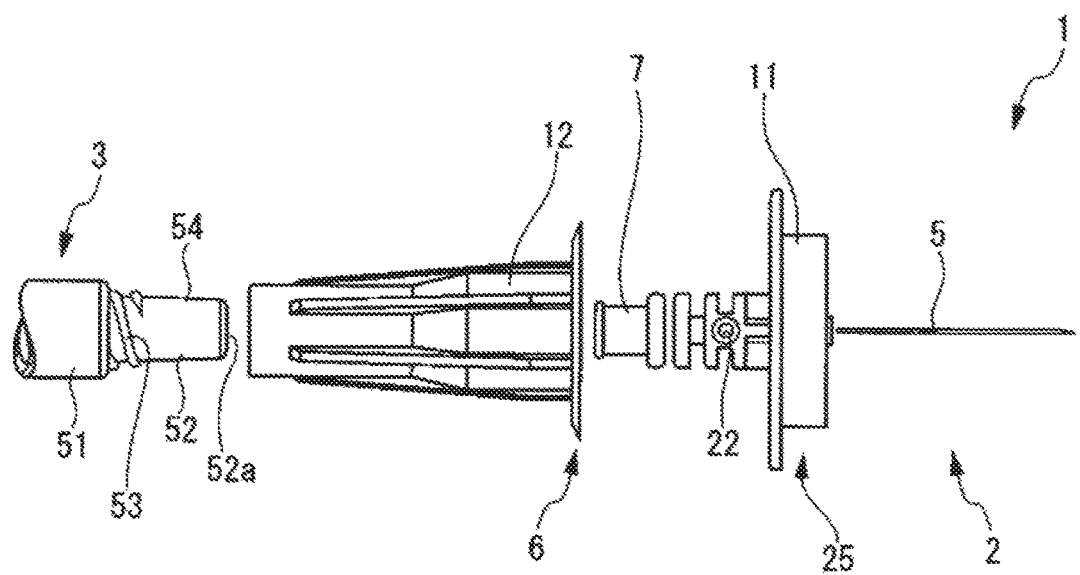
FIG. 2 is an exploded view showing the first exemplary embodiment of the medicine injection device according to the disclosure herein.

As shown in FIG. 2, the injection needle assembly 2 includes: a hollow needle tube 5 having a needle hole; a needle hub 6 to which the needle tube 5 is fixed; and an elastic member 7 disposed inside of the needle hub 6. Further, the needle hub 6 includes: a first member 11 that is a retention part for retaining the needle tube 5; and a second member 12 that is a connector part to which the syringe 3 is connected.

The above described individual components of the medicine injection device 1 are described below with reference to FIG. 3.

The needle tube 5 of the injection needle assembly 2 preferably includes a needle tube of the size of 22 to 33-gauge (i.e., an outer diameter of 0.2 to 0.7 mm), compliant to the ISO standard for a needle tube for medicine (Ref: ISO 9626: 1991/Amd. 1: 2001 (E)). A 26 to 33-gauge, or preferably a 30 to 33-gauge, can of course also be used for injecting into an upper skin layer.

One end of the needle tube 5 is provided with a needle tip 5A having a blade surface 5a. The other end of the needle tube 5 in the axial direction on an end opposite to the needle tip 5A is referred to as a base end 5B hereinafter. A length of the needle tube 5 on the blade surface 5a in the axial direction (noted as 'bevel length B' hereinafter) may be 1.4 mm or less, which is equivalent to the smallest thickness of an upper skin layer (for adults), and may be 0.5 mm or more, which is a bevel length in a case where a short bevel is formed on a 33-gauge needle tube. That is, the bevel length B is preferably set in a range of 0.5-1.4 mm.

Furthermore, the bevel length B is more preferably set in a range of 0.5-0.9 mm, considering that the minimum thickness of the upper skin layer may be 0.9 mm or less (for infants), it is noted that the short bevel represents a blade surface inclined by an angle of 18 to 25 degrees relative to the longitudinal direction of a needle that is commonly used for an injecting needle. The surface of the needle tip 5A of the needle tube 5 is preferably coated with a coating agent made of, for example, a silicon resin, a fluorine series resin or the like. This configuration makes it possible to reduce friction between the skin and needle tube 5 when a living body is punctured with the needle tube, thus enabling reduction in the pain associated with the puncture.

A preferred material for the needle tube 5 may be, for example, stainless steel. Aluminum, aluminum alloy, titanium, titanium alloy or other material may also be used. The needle tube 5 may be a straight needle, or a taper needle that has a taper structure for at least a part of the needle may also be used. With respect to a taper needle, there is a possible configuration that has a larger diameter at a base portion compared to that at the needle tip portion, with the middle part having a taper configuration. The needle tube 5 may have a cross-sectional form of not only a circle, but also a polygon such as, for example, a triangle. The needle tube 5 is fixed to the needle hub 6.

The first member 11 and second member 12 of the needle hub 6 are preferably formed as separate members. However, they may be formed as an integrated member. The first member 11 and second member 12 may be made of a synthetic resin such as, for example, polycarbonate, polypropylene, or polyethylene.

The first member 11 is provided with a skin contact portion 25 that makes contact with and/or faces the skin. The skin contact portion 25 is disposed in a manner so as to cover the area surrounding the needle tube 5 when the needle tube 5 is attached to the first member 11. The skin contact portion 25 includes a substantially columnar base part 15, an adjustment portion 16, a stabilizer 17, and a guide portion 18. As described herein, one side of the base part 15 in the axial direction and the adjustment portion 16 constitute a front end part of the exemplary embodiment of the disclosed device.

The base part 15 has end faces 15a and 15b that are orthogonal to the axial direction. The adjustment portion 16 is disposed at a center portion of the end face 15a on one end of the base part 15 in the axial direction and includes a columnar convex portion protruding in the axial direction of the base part 15. The center shaft of the adjustment portion 16 coincides with that of the base part 15.

The center shaft of the base part 15 and adjustment portion 16 is provided with a through hole 21 through which the needle tube 5 extends. Further, the base part 15 is provided with an introduction hole 22 (see FIG. 2) for introducing an adhesive 20 (see FIG. 3) into the through hole 21. The introduction hole 22 is open into an outer peripheral surface of the base part 15 and communicates with the through hole 21 in a manner substantially orthogonal thereto. That is, the needle tube 5 is adhesively fixed to the base part 15 by the adhesive 20 introduced into the through hole 21 from the introduction hole 22.

The base end 5B side of the needle tube 5 protrudes from the end face 15b that is the other end of the base part 15 in the axial direction. The base part 15 is inserted into the second member 12 from the end face 15b side, while the base end 5B side of the needle tube 5 is inserted into a through hole 45 (described later) of the elastic member 7. The end face 15b of the base part 15 thus abuts an end face 41a of the elastic member 7.

Further, a connecting flange 24 is provided on the outer circumferential surface of the base part 15. The connecting flange 24 is formed as a ring-like flange protruding outwardly in the radial direction from the base part 15 and has flat surfaces 24a and 24b that are opposite to each other in the axial direction of the base part 15. The second member 12 is connected to the flat surface 24b of the connecting flange 24. An edge portion of the connecting flange 24 also constitutes a guide portion 18, as described in detail below.

The end face of the adjustment portion 16 defines a needle protrusion surface 16a from which the needle tip 5A side of the needle tube 5 protrudes. The needle protrusion surface 16a is formed as a flat surface orthogonal to the axial direction of the needle tube 5. The needle protrusion surface 16a contacts a skin surface and regulates the depth of puncture of the needle tube 5 when an upper skin layer is punctured with the needle tube 5. In other words, the depth of the puncture of the needle tube 5 into the upper skin layer is determined by the length of the needle tube 5 (noted as "protruding length L" hereinafter) protruding from the needle protrusion surface 16a.

The thickness of an upper skin layer is equivalent to the depth from a skin surface to the dermis layer and falls approximately in a range of 0.5-3.0 mm. Therefore, the protruding length L of the needle tube 5 preferably can be set in a range of 0.5-3.0 mm.

A vaccine is generally administered in an upper arm region. When considering administration to the upper skin layer, however, it is appropriate to administer in a shoulder region; particularly at the triangular muscle region, where the skin is generally thick. The thickness of the upper skin layer of the triangular muscle has been individually measured on 19 infants and 31 adults. The measurements have been made by using an ultrasonic measurement apparatus (NP60R-UBM; high definition imaging echo for small animals; Nepa Gene Co., Ltd) and imaging the upper skin layer where ultrasonic reflectivity is high. Logarithmic normal distribution is constituted by the measurement values, and therefore a range of MEAN±2SD has been calculated by a geometric mean method.

As a result; the thickness range of the upper skin layer of the triangular muscle for infants is determined to be between 0.9 and 1.6 mm. Further, the thickness ranges of the upper skin layer of the triangular muscle for adults determined to be: between 1.4 and 2.6 mm at the distal portion; between 1.4 and 2.5 mm at the central portion; and between 1.5 and 2.5 mm at the proximal portion. This result has confirmed that the thickness of the upper skin layer at the triangular muscle is 0.9 mm or larger for infants, and 1.4 mm or larger for adults. Therefore, it is desirable to set the protruding length L of the needle tube 5 in a range of 0.9-1.4 mm for injection in the upper skin layer of a triangular muscle.

Having thus determined the protruding length L makes it possible to securely position the blade surface 5a of the needle tip 5A in the upper skin layer. This, in turn, makes it possible to position the needle opening (i.e., medicine fluid output port) that opens into the blade surface 5a at the upper skin layer, no matter where the needle opening is located within the blade surface 5a. It will be appreciated that it is important for the blade surface 5a to be firmly positioned at the upper skin layer. That is, a deep puncture of the needle tip 5A into the upper skin layer will cause the medicine fluid to flow into a subcutaneous layer due to a gap between a side surface of the end portion of the needle tip 5A and the cut skin, even if the medicine fluid output port is positioned at the upper skin layer.

In the case of using a needle tube for administration into the upper skin layer, it is very difficult to configure the bevel length B at 1.0 mm or smaller when a needle tube larger than 26-gauge is used. Therefore, it is desirable to use a needle tube smaller than 26-gauge in order to set the protruding length L of the needle tube 5 in a preferable range (i.e., 0.9 to 1.4 mm).

The needle protrusion surface 16a is formed so that the distance S from the circumferential edge thereof to the circumferential surface of the needle tube 5 will be 1.4 mm or less (more preferably in a range of 0.3-1.4 mm). The distance S from the circumferential edge of the needle protrusion surface 16a to the circumferential surface of the needle tube 5 is determined in consideration of the pressure exerted on a fluid bubble that is formed when administering a medicine to the upper skin layer. That is, the needle protrusion surface 16a is set at a size that is sufficiently smaller than a bubble formed in the upper skin layer, and thus allows the forming of a bubble. As a result, it possible to prevent the needle protrusion surface 16a from pressing the skin surrounding the needle tube 5 and thereby prevent leaking of the administered medicine.

The stabilizer 17 is cylindrically formed to protrude from the flat surface 24a of the connecting flange 24 disposed on the base part 15. The cylindrical opening of the stabilizer 17 is provided with the needle tube 5 and the adjustment portion 16. That is, the stabilizer 17 forms a cylinder covering the area surrounding the adjustment portion 16 in which the needle tube 5 is inserted, and is disposed at a distance spaced from the needle tip 5A of the needle tube 5 in the radial direction.

Figure 3:
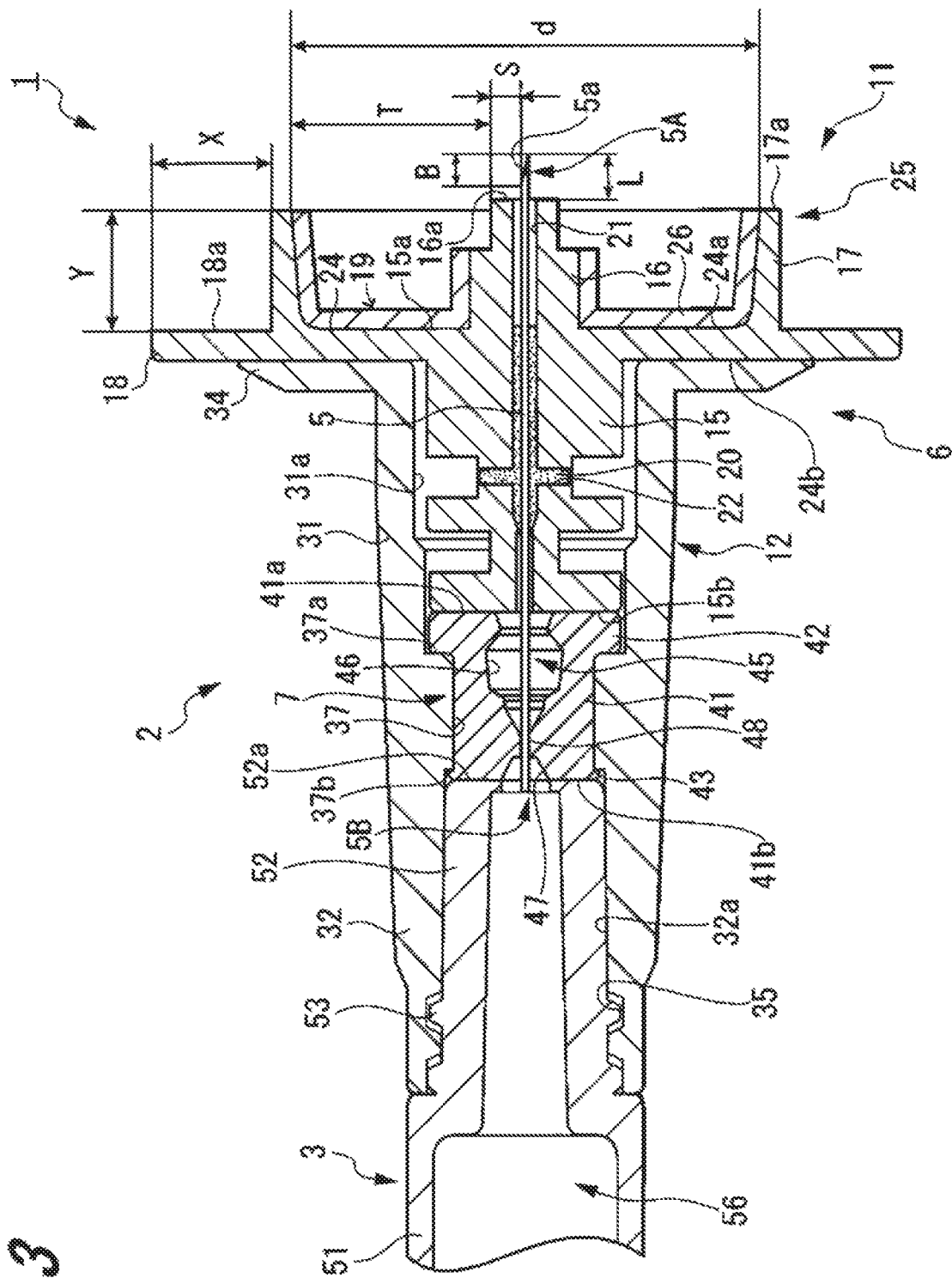
FIG. 3 is a cross-sectional view showing the first exemplary embodiment of the medicine injection device according to the disclosure herein.

As shown in FIG. 3, the end face 17a of the stabilizer 17 is disposed at a position shifted toward the base end 5B of the needle tube 5 relative to the needle protrusion surface 16a of the adjustment portion 16. As a living body is punctured with the needle tip 5A of the needle tube 5, the needle protrusion surface 16a makes contact with the skin surface first, and then, with the end face 17a of the stabilizer 17. The end face 17a of the stabilizer 17 contacting the skin stabilizes the orientation of the medicine injection device 1, and thereby makes it possible to maintain the orientation of the needle tube 5 substantially orthogonal to the skin.

Alternatively, the end face 17a of the stabilizer 17 would also make it possible to maintain the needle tube 5 at an orientation substantially orthogonal to the skin even if the end face 17a was positioned at the same plane as the needle protrusion surface 16a or if the end face 17a was positioned at a position shifted toward the needle tip 5A side of the needle tube 5 from the needle protrusion surface 16a. The distance between the end face 17a of the stabilizer 17 and the needle protrusion surface 16a in the axial direction thereof is preferably 1.3 mm or less in consideration of a bump on the skin caused by pressing the stabilizer 17 onto the skin.

The internal diameter d of the stabilizer 17 is set at a value equivalent to, or larger than, the diameter of a fluid bubble formed on the skin. Specifically, the diameter d is so set that the distance T from the inner wall surface of the stabilizer 17 to the circumferential edge of the needle protrusion surface 16a falls in a range of 4 to 15 mm. This configuration makes it possible to assure formation of a bubble by preventing application of pressure from the inner wall surface of the stabilizer 17 to the bubbles.

The smallest distance T from the inner wall surface of the stabilizer 17 to the outer circumferential surface of the adjustment portion 16 may be discretionarily increased, provided that it is 4 mm or greater. However, as the distance T is increased, the outer diameter of the stabilizer 17 is increased, making it increasingly difficult to cause the entirety of the end face 17a of the stabilizer 17 to contact the skin when the needle tube 5 penetrates a thin arm, such as an infant's. Therefore, the distance T is preferably set at a maximum of 15 mm in consideration of the thinness of infants' arms.

Further, provided that the distance S from the circumferential edge of the needle protrusion surface 16a to the circumferential surface of the needle tube 5 is 0.3 mm or more, the adjustment portion 16 will never invade the skin. Therefore, taking into consideration the distance T (4 mm or larger) from the inner wall surface of the stabilizer 17 to the circumferential edge of the needle protrusion surface 16a and the diameter (about 0.3 mm) of the needle protrusion surface 16a, the internal diameter d of the stabilizer 17 can preferably be 9 mm or larger.

It will be appreciated by one skilled in the art that the form of the stabilizer 17 is not limited to a circular cylindrical shape as illustrated; it may be formed to have a square cylindrical shape, such as a rectangular column or hexagonal column, with a cylindrical hole bored at the center.

The guide portion 18 is positioned on an outer side of the first member 11, extending further in the radial direction than the stabilizer 17 of the connecting flange 24. The guide portion 18 has a contact surface 18a that contacts the skin. The contact surface 18a is a part of the flat surface 24a of the connecting flange 24 and is a flat surface substantially parallel to the end face 17a of the stabilizer 17. Pressing on the stabilizer 17 until the contact surface 18a of the guide portion 18 contacts the skin makes it possible to apply a force at a predetermined value, the force with which the stabilizer 17 and the needle tube 5 press the skin. With this configuration, a part of the needle tube 5 protruding from the needle protrusion surface 16a (equivalent to the protruding length L) is securely penetrated into the skin.

The distance Y (noted as "guide portion height" hereinafter) from the contact surface 18a of the guide portion 18 to the end face 17a of the stabilizer 17 is set at a length to allow the needle tube 5 and the stabilizer 17 to press the skin with the correct pressing force so as to puncture the skin. In the exemplary embodiment of the disclosure, the correct pressing force of the needle tube 5 and the stabilizer 17 is, for example, 3 to 20 N. This configuration enables a user to cause the guide portion 18 to control the pressing force exerted to the skin by the needle tube 5 and the stabilizer 17, making it possible to securely position the needle tip 5A (i.e., the blade surface 5a) of the needle tube 5 in the upper skin layer and provide the user with a feeling of ease.

The guide portion height Y is appropriately determined on the basis of the internal diameter d of the stabilizer 17 and the length X (noted as "guide portion length" hereinafter) from the edge surface of the guide portion 18 to the outer peripheral surface of the stabilizer 17. For example, in a case where the internal diameter d of the stabilizer 17 is 12 mm while the guide portion length X is 3.0 mm, the guide portion height Y is set in a range of 2.3-6.6 mm.

The adjustment portion 16 and stabilizer 17 of the skin contact portion 25 form a concave portion 19. The concave portion 19 is provided with a fluid-draining portion 26. The fluid-draining portion 26 is formed by coating the concave portion 19 with a lubricant. This configuration causes a medicine that has been spilled from the needle tube 5 during air removal to be repelled when the fluid is received in the fluid-draining portion 26, instead of being attached to the concave portion 19, and thereby enabling the user to easily drain the fluid by tipping the skin contact portion 25 or like action. Furthermore, the configuration makes it possible to prevent the medicine that has spilled from the needle tube 5 from contacting or attaching to the user since it is held in the concave portion 19. In a preferred exemplary embodiment of the disclosure, silicon- or fluorine coating and the like can be used for a lubricant in forming the fluid-draining portion 26.

The second member 12 is formed substantially cylindrical. One end of the second member 12 in the axial direction constitutes an insertion portion 31 into which the base part 15 of the first member 11 is inserted, while the other end constitutes a coupling portion 32 configured to be coupled with an output portion 52 (described later) of the syringe 3. A cylindrical hole 31a of the insertion portion 31 is set at a size corresponding to the base part 15 of the first member 11.

The insertion portion 31 is provided with a fixing flange 34 that is configured for connecting to the connecting flange 24 of the first member 11. The fixing flange 34 is formed as a ring-like flange projecting in the radial direction continuously from the end of the insertion portion 31. The fixing flange 34 is abutted, and fixed, to the flat surface 24b of the connecting flange 24 of the first member 11. A method of fixing the fixing flange 34 to the connecting flange 24 can include, for example, an adhesive, ultrasonic welding, laser welding, and fastening screws.

The cylindrical hole 32a of the coupling portion 32 is set at a size corresponding to the output portion 52 of the syringe 3, with the diameter of the cylindrical hole 32a decreasing toward the insertion portion 31 side. The coupling portion 32 is provided on its internal surface with a groove 35 formed for threadedly engaging the output portion 52 of the syringe 3.

An engagement portion 37 is disposed between the insertion portion 31 and the coupling portion 32. The engagement portion 37 is configured to be engaged with the elastic member 7. The engagement portion 37 is formed as a step portion protruding inwardly in the radial direction from the inner surface of the second member 12 and has engagement surfaces 37a and 37b that are substantially orthogonal to the axial direction of the second member 12. The engagement surface 37a of the engagement portion 37 engages a flange portion 42 (described later) of the elastic member 7, while the engagement surface 37b engages a stopper protrusion portion 43 of the elastic member 7.

The elastic member 7 is disposed inside of the second member 12 of the needle hub 6 and is positioned between the first member 11 and the syringe 3. The elastic member 7 includes: a body part 41; a flange portion 42 provided on one end of the body part 41 in the axial direction; and a stopper protrusion portion 43 provided on the other end of the body part 41.

The body part 41 is substantially columnar and has end faces 41a and 41b that are orthogonal to the axial direction. The end face 41a of the body part 41 abuts with the end face 15b of the base part 15 of the first member 11 while the end face 41b abuts in a fluid-tight manner with a tip end of the output portion 52 provided on the syringe 3. That is, the end face 41b constitutes an abutting surface where the tip end of the output portion 52 is fluid-tightly abutted.

The body part 41 is provided with a through hole 45 for allowing insertion of the base end 5B side of the needle tube 5 protruding from the end face 15b of the base part 15. The through hole 45 extends in the axial direction of the body part 41 and opens into the end faces 41a and 41b. The inner surface of the body part 41 includes an end face-side separation portion 46, an abutment surface-side separation portion 47, and a close contact portion 48.

The end face-side separation portion 46 forms an opening of the through hole 45 on the end face 41a. The end face-side separation portion 46 is spaced from the outer circumferential surface of the needle tube 5 and has a tapered form in which the diameters of the through hole 45 continuously increase toward the end face 41a. This configuration makes it possible to easily insert, into the through hole 45, the base end 5B side of the needle tube 5 protruding from the end face 15b of the base part 15. It is appreciated by one skilled in the art that the end face-side separation portion 46 of the through hole 45 may have an alternative form, provided that it allows easy insertion of the needle tube 5 into the through hole 45.

The abutment surface-side separation portion 47 forms an opening of the through hole 45 on the end face 41b. The abutment surface-side separation portion 47 is separated or spaced from the outer circumferential surface of the needle tube 5 and has a tapered form in which the diameter of the through hole 45 continuously increase toward the end face 41b. The provision of the abutment surface-side separation portion 47 to the elastic member 7 makes it possible to prevent the end face 41b side of the body part 41 from deforming and thereby covering the base end 5B of the needle tube 5 and blocking the needle hole.

The abutment surface-side separation portion 47 of the through hole 45 is not limited to a tapered form. For example, it may be a concave portion that has a diameter larger than the diameter of the close contact portion 48 and is separated from the outer circumferential surface of the needle tube 5. In other words, the abutment surface-side separation portion 47 of the through hole 45 may have any form, provided that it is capable of preventing the body part 41 from deforming on the end face 41b side, covering the base end 5B of the needle tube 5, and blocking the needle hole.

The close contact portion 48 is formed between the end face-side separation portion 46 and the abutment surface-side separation portion 47. The close contact portion 48 contacts the outer circumferential surface of the needle tube 5 in a fluid-tight manner. This configuration makes it possible to prevent invasion of the medicine inside of the syringe 3 into the first member 11 side of the needle hub 6 from a gap between the needle tube 5 and the elastic member 7.

The flange portion 42 has a ring-like shape protruding in the radial direction from the outer circumferential surface of the body part 41. The outer diameter of the flange portion 42 is substantially the same as the outer diameter of the base part 15 of the first member 11. Therefore, one flat surface of the flange portion 42 abuts the engagement surface 37a of the engagement portion 37 disposed in the second member 12, while the other flat surface abuts the end face 15b of the base part 15 of the first member 11. The elastic member 7 is attached to the needle hub 6 by the engagement portion 37 of the second member 12 and the base part 15 of the first member 11 sandwiching the flange portion 42.

The stopper protrusion portion 43 is formed in a ring-like shape protruding outwardly in the radial direction from the outer circumferential surface of the body part 41, similar to the form of the flange portion 42. The stopper protrusion portion 43 is engaged with the engagement surface 37b of the engagement portion 37 disposed on the second member 12. The elastic member 7 is thus locked from moving in an axial direction by the flange portion 42 and the stopper protrusion portion 43 engaging with the engagement portion 37 of the second member 12.

For the elastic member 7, various elastomeric materials such as natural rubber and silicone elastomer, various elastomeric materials such as urethane series and styrene series, or elastic materials made from a mixture of them may be used.

The syringe 3 includes a syringe body 51, and an output portion 52 that continues to the syringe body 51. The syringe body 51 has a circular cylindrical body. The output portion 52 protrudes from one end of the syringe body 51 in the axial direction and has a circular cylindrical body with a smaller diameter than that of the syringe body 51. The output portion 52 has a tapered form whose diameter continuously decreases toward the tip end. An end face 52a constituting the tip end of the output portion 52 is a flat surface orthogonal to the axial direction and fluid-tightly abuts to the end face 41b of the elastic member 7. Further, the outer circumferential surface of the output portion 52 is provided with a screw threaded portion 53 for threadably connecting with the second member 12 of the needle hub 6.

The syringe body 51 internally houses a gasket (not shown in a drawing). A space inside of the syringe body 51 is sectioned by the gasket so that one space communicating with the output portion 52, together with the space inside of the output portion 52, forms a fluid chamber 56. A plunger (not shown in a drawing) is disposed in the other space inside of the syringe body 51. The plunger is connected to the gasket and protrudes from an opening at the other end of the syringe body 51. An operation of the plunger moves the gasket in the axial direction inside of the syringe body 51, performing suction of a medicine into the fluid chamber 56 and outputting of the medicine filled in the fluid chamber 56.

A synthetic resin such as polycarbonate, polypropylene, and polyethylene, or a metallic material such as stainless steel and aluminum may be used for the material of the syringe body 51 and the output portion 52.

A method of using the medicine injection device 1 is described below.

First, a user exhausts the air contained inside of the syringe 3 of an assembled medicine injection device 1, that is, the user performs the air removal procedure. This operation causes a medicine M to be spilled from the needle tip 5A of the needle tube 5 during air removal as shown by the illustrated droplets in FIG. 4A. The medicine M that has been spilled from the needle tip 5A drops into the concave portion 19 formed by the adjustment portion 16 and the stabilizer 17 to stay in the fluid-draining portion 26. The fluid-draining portion 26 includes a lubricant, and therefore the medicine M that has been spilled from the needle tip 5A is repelled from the concave portion 19 instead of being attached thereto. Therefore, the user is able to easily drain the medicine M staying in the fluid-draining portion 26 by tipping the medicine injection device 1, as shown in FIG. 4B.

The end face 17a of the stabilizer 17 is then placed adjacent to a skin in order to puncture a living body with the needle tip 5A of the needle tube 5. This operation causes the needle tip 5A of the needle tube 5 to face the skin to be punctured. The medicine injection device 1 is moved substantially orthogonally to the skin, the skin is punctured with the needle tip 5A, and simultaneously the end face 17a of the stabilizer 17 is pressed against the skin. In this event, the needle protrusion surface 16a contacts the skin to deform it flatly, making it possible to puncture the skin with the needle tip 5A of the needle tube 5 for a depth equivalent to the protrusion length L.

The end face 17a of the stabilizer 17 is pressed until the contact surface 18a of the guide portion 18 makes contact with the skin. The guide height Y is set so that the skin can be punctured with the needle tube 5 and the stabilizer 17 with an appropriate magnitude of pressing force. Therefore, the force pressing the skin is maintained at a predetermined value by the stabilizer 17.

As a result, the configuration enables the user to recognize the appropriate pressing force for the stabilizer 17 and to securely position the needle tip 5A and blade surface 5a of the needle tube 5 in the upper skin layer. As described above, the guide portion 18 functions as an indicator for the user to recognize the appropriate magnitude of pressing force of the stabilizer 17, allowing him to comfortably use the medicine injection device 1.

The stabilizer 17 abutting the skin also stabilizes the orientation of the medicine injection device 1, enabling straight puncture of the skin with the needle tube 5. It is also possible to prevent a wobbling of the needle tube 5 after the puncturing, thus enabling stable administration of the medicine.

The possibility exists of being unable to puncture a skin with a needle tip after it is abutted to the skin in a case where a needle tube has, for example, an extremely short protrusion length such as about 0.5 mm. However, the skin, when pressed by the stabilizer 17, is pushed down in the orthogonal direction, expanding the skin inside of the stabilizer 17, and thereby generating tension in the skin. This state makes it difficult for the skin to escape from the needle tip 5A of the needle tube 5. Therefore, the provision of the stabilizer 17 also renders a benefit for easy puncturing of the skin with the needle tip 5A.

After the skin is punctured with the needle tip 5A side of the needle tube 5, the plunger (not shown in a drawing) is pressed to move the gasket (not shown in a drawing) to a side where the output portion 52 exists. Accordingly, the medicine filled in the fluid chamber 56 of the syringe 3 is pushed out from the output portion 52, pushed through the needle hole of the needle tube 5 and injected into the upper skin layer from the needle tip 5A. In this event, no space is formed between the tip end of the output portion 52 and the base end 5B of the needle tube 5, and therefore a residual amount of the medicine can be reduced.

A second exemplary embodiment of the injection needle assembly according to the disclosure is described with reference also to FIG. 5. An injection needle assembly 62 according to the second exemplary embodiment is configured similarly to the injection needle assembly 2 of the first exemplary embodiment. Where the injection needle assembly 62 according to the second exemplary embodiment differs from the injection needle assembly 2 of the first exemplary embodiment is only a fluid-draining portion 66. Accordingly, the fluid-draining portion 66 is described here. Other components common to the injection needle assembly 2 are indicated with the same reference numerals, and no duplicate description is provided.

Figure 5:
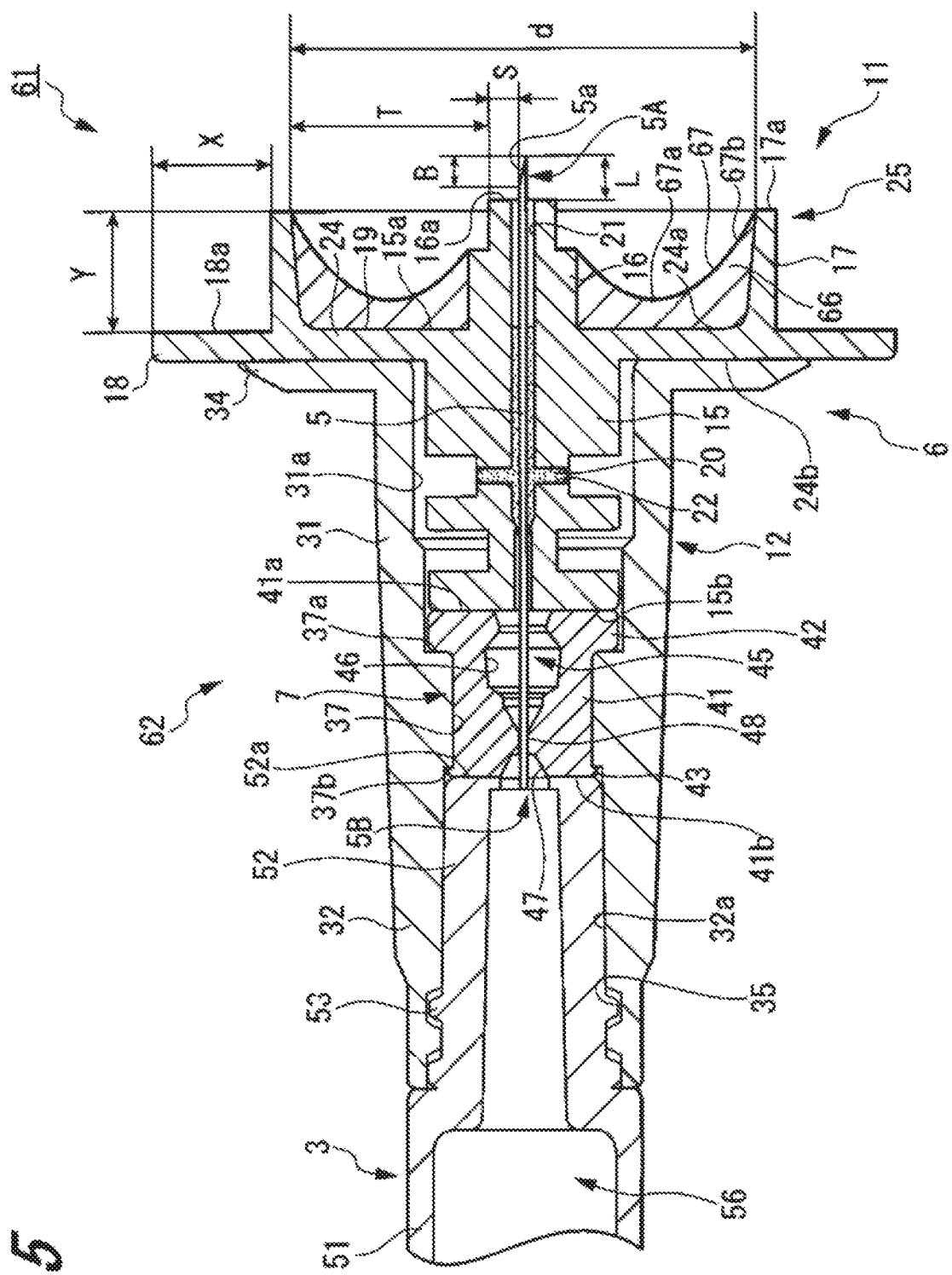
FIG. 5 is a cross-sectional view showing a second exemplary embodiment of the medicine injection device according to the disclosure herein.

As shown in FIG. 5, the fluid-draining portion 66 is provided in a concave portion 19 that is formed by the adjustment portion 16 and stabilizer 17 of the skin contact portion 25. The fluid-draining portion 66 is provided with a fluid-draining concave portion 67 that is formed with a curved concave shape that is recessed toward the insertion portion 31 of the needle hub 6.

In the fluid-draining concave portion 67, a middle point between the adjustment portion 16 and stabilizer 17 defines the greatest recessed area, and thus the middle point constitutes a bottom portion 67a of the fluid-draining concave portion 67. The fluid-draining concave portion 67 has a concave shape continuously climbing toward the adjustment portion 16 and the stabilizer 17 from the bottom portion 67a. This configuration forms a sloped surface 67b inclined upward from the bottom portion 67a of the fluid-draining concave portion 67 toward the stabilizer 17 that is the edge of the skin contact portion 25.

The fluid-draining portion 66 is disposed in the concave portion 19 formed by the adjustment portion 16 and the stabilizer 17, and therefore the fluid-draining portion 66 is sized corresponding to the size of the concave portion 19. Further, a synthetic resin such as polycarbonate, polypropylene and polyethylene can be used as the material for a member having the curved configuration of the fluid-draining portion 66.

The fluid-draining portion 66 is curvedly formed, and therefore a medicine that has been spilled during air removal is held in the bottom portion 67a of the fluid-draining concave portion 67. Further, there is no corner in the fluid-draining portion 66, and therefore a user is able to drain the medicine staying in the fluid-draining portion 66 by tipping the medicine injection device 61, causing the medicine to flow along the sloped surface 67b. Accordingly, it is possible to prevent the medicine that has been spilled during air removal from attaching to or contacting the user.

An exemplary embodiment in which the fluid-draining portion 66 and the skin contact portion 25 are configured as separate members has been described above relative to the second embodiment. The disclosure, however, is not limited by the configuration described above, and for example, the fluid-draining portion 66 may be integrally molded when the first member 11 is molded.

Further, the curved surface of the fluid-draining portion 66 of the second exemplary embodiment may be coated with a lubricant. This configuration makes it possible to realize improvement in a fluid repellent effect and facilitate draining of the medicine staying in the fluid-draining portion 66.

Other configurations of the second exemplary embodiment are the same as the injection needle assembly 2 of the first exemplary embodiment, and therefore no description for them is given here. Use of such a configured injection needle assembly 62 also makes it possible to realize the same function and effectiveness as the injection needle assembly 2 of the first exemplary embodiment described above.

It is appreciated that the disclosure here is no way limited to the exemplary embodiments that have been described and shown in the accompanying drawings. The disclosure may be modified for embodiments in various modes within the scope and spirits of the invention noted in the claims herein. For example, an exemplary embodiment configured to dispose an elastic member between the first member and the second member has been described herein. However, an injection needle assembly may be configured without disposing such elastic member, or alternatively be configured to integrally form a second member and an elastic member.

It is also noted that the medicine injection device according to the disclosure is applied to an intracutaneous injection. The disclosure, however, is not limited to such application. For example, the medicine injection device may be applied to a subcutaneous injection and an intramuscular injection, with adjustment of the protrusion length of the medicine injection device.

The detailed description above describes features, characteristics and operational aspects of embodiments of an injection needle assembly and medicine injection device representing examples of the injection needle assembly and medicine injection disclosed herein. The disclosure and the present invention are not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. A method of using a medicine injection device comprising a syringe filled with a medicine and having an output portion; a needle tube having a needle tip for puncturing the skin; a needle hub including a retention part for retaining the needle tube and an insertion part into which an output portion of the syringe is inserted; a flange-like skin contact portion that is disposed in a manner so as to cover an area surrounding the needle tube and makes contact with and/or faces the skin when the living body is punctured with the needle tube, the flange-like skin contact portion comprising an adjustment portion that is disposed in an area surrounding the needle tube and includes a needle protrusion surface from which the needle tip of the needle tube protrudes, and a cylindrically formed stabilizer that is disposed in a manner so as to cover an area surrounding the needle tube and makes contact with skin when a living body is punctured with the needle tube; and a fluid-draining portion that is disposed in the flange-like skin contact portion of the needle hub, said method comprising:

removing air from the medicine injection device prior to injection of the medicine, whereby medicine spilled from the needle tip is caught in the fluid-draining portion;

draining the spilled medicine in the fluid-draining portion by tipping the medicine injection device;

positioning the flange-like skin contact portion adjacent the skin, the positioning of the flange-like skin contact portion adjacent the skin including placing an end face of the stabilizer adjacent the skin such that needle tip of the needle tube is facing the skin to be punctured;

puncturing the skin with the needle tip; and injecting medicine from the needle tip into the skin.

2. The method according to claim 1, wherein the fluid-draining portion includes a lubricant, the fluid-draining portion repelling the spilled medicine.

3. The method according to claim 1, further comprising pressing the end face of the stabilizer against the skin.

4. The method according to claim 3, further comprising the needle protrusion surface contacting the skin and deforming the skin with the needle protrusion surface.

5. The method according to claim 1, wherein the flange-like skin contact portion further comprises a guide portion that is disposed on an outer circumferential surface of the stabilizer and makes contact with the skin when the living body is punctured with the needle tube, thereby guiding a pressing force of both the needle tube and the stabilizer and defining the force to be exerted to the living body.

6. The method according to claim 3, wherein the flange-like skin contact portion further comprises a guide portion that is disposed on an outer circumferential surface of the stabilizer, said method further comprising pressing the end face of the stabilizer against the skin until a contact surface of the guide portion makes contact with the skin.

7. The method according to claim 6, further comprising maintaining the force pressing the skin at a predetermined value with the stabilizer.

8. The method according to claim 1, wherein the fluid-draining portion is disposed in a concave portion formed by the adjustment portion and the stabilizer, wherein medicine spilled from the needle tip and caught in the fluid-draining portion includes catching medicine in the concave portion.

9. The method according to claim 1, wherein injecting medicine from the needle tip into the skin includes pushing medicine from a fluid chamber of the syringe to the output portion of the syringe.

* * * * *